(12) United States Patent
Hu et al.

(10) Patent No.: US 10,060,901 B2
(45) Date of Patent: Aug. 28, 2018

(54) CONCRETE TEMPERATURE STRESS TESTING MACHINE SYSTEM AND TEMPERATURE DEFORMATION SELF-COMPENSATION METHOD

(71) Applicants: Tsinghua University, Beijing (CN); CHANGCHUN CITY CHAOYANG TEST INSTRUMENTS CO., LTD., Changchun (CN)

(72) Inventors: Yu Hu, Beijing (CN); Qingbin Li, Beijing (CN); He Zhu, Beijing (CN); Ge Wang, Changchun (CN)

(73) Assignees: TSINGHUA UNIVERSITY, Beijing (CN); CHANGCHUN CITY CHAOYANG TEST INSTRUMENTS CO., LTD., Changchun (CN)

( * ) Notice: Subject to any disclaimer, the term of this patent is extended or adjusted under 35 U.S.C. 154(b) by 0 days.

(21) Appl. No.: 15/855,526

(22) Filed: Dec. 27, 2017

(65) Prior Publication Data
US 2018/0120284 A1    May 3, 2018

Related U.S. Application Data

(63) Continuation of application No. 15/404,338, filed on Jan. 12, 2017, now Pat. No. 9,891,208.

(30) Foreign Application Priority Data

Jul. 8, 2016  (CN) ........................ 2016 1 0539510
Jul. 8, 2016  (CN) .................... 2016 2 0722524 U
(Continued)

(51) Int. Cl.
*G01N 33/38*   (2006.01)
*G01N 3/02*    (2006.01)
*G01B 21/32*   (2006.01)

(52) U.S. Cl.
CPC .......... *G01N 33/383* (2013.01); *G01B 21/32* (2013.01); *G01N 3/02* (2013.01);
(Continued)

(58) Field of Classification Search
CPC ................. G01N 33/383; G01N 3/02; G01N 2203/0092; G01N 2203/0222; G01N 2203/0246; G01B 21/32
(Continued)

(56) References Cited

U.S. PATENT DOCUMENTS

| | | | | | |
|---|---|---|---|---|---|
| 3,603,141 | A | * | 9/1971 | Kinkead ................. | G01B 5/30 73/785 |
| 5,365,793 | A | * | 11/1994 | Terrel ...................... | G01N 3/36 73/38 |
| 5,571,951 | A | * | 11/1996 | Jamth .................. | G01N 33/383 73/53.01 |

FOREIGN PATENT DOCUMENTS

| CN | 2906546 Y | 5/2007 |
|---|---|---|
| CN | 200962108 Y | 10/2007 |

(Continued)

OTHER PUBLICATIONS

SIPO, Office Action for CN application 201610539510.5 dated Nov. 3, 2017.

(Continued)

*Primary Examiner* — Max Noori
(74) *Attorney, Agent, or Firm* — Hodgson Russ LLP

(57) ABSTRACT

A concrete temperature stress testing machine system and a testing method are provided, in which the concrete temperature stress testing machine system includes: a concrete temperature stress testing machine and a walk-in environment simulation laboratory system; and the concrete temperature stress testing machine includes a testing machine host and a concrete test specimen area. The testing machine host includes a rear fixed end, a front fixed end, and a pair of steel shafts connected between the rear fixed end and the front fixed end. The concrete test specimen area includes a moveable cross-head, a fixed cross-head, and a left side (Continued)

formwork, a bottom formwork and a right formwork connected between the moveable cross-head and the fixed cross-head.

8 Claims, 3 Drawing Sheets

(30) Foreign Application Priority Data

| | | |
|---|---|---|
| Aug. 4, 2016 | (CN) | 2016 1 0630276 |
| Aug. 4, 2016 | (CN) | 2016 1 0630280 |
| Aug. 4, 2016 | (CN) | 2016 1 0632642 |
| Aug. 4, 2016 | (CN) | 2016 2 0835554 U |
| Aug. 4, 2016 | (CN) | 2016 2 0836473 U |
| Aug. 4, 2016 | (CN) | 2016 2 0838657 U |

(52) U.S. Cl.
CPC ........... *G01N 2203/0092* (2013.01); *G01N 2203/0222* (2013.01); *G01N 2203/0246* (2013.01)

(58) Field of Classification Search
USPC .......................................... 73/803
See application file for complete search history.

(56) References Cited

FOREIGN PATENT DOCUMENTS

| | | |
|---|---|---|
| CN | 101245991 A | 8/2008 |
| CN | 201149484 Y | 11/2008 |
| CN | 201203404 Y | 3/2009 |
| CN | 205941547 U | 2/2017 |

\* cited by examiner

CONCRETE TEMPERATURE STRESS TESTING MACHINE SYSTEM AND TEMPERATURE DEFORMATION SELF-COMPENSATION METHOD

CROSS-REFERENCE TO RELATED APPLICATION

The present application is a continuation of U.S. patent application Ser. No. 15/404,338, with a filing date of Jan. 12, 2017, the entire disclosure of which is incorporated herein by reference.

FIELD

The present disclosure belongs to a field of construction industry and relates to a concrete temperature stress testing machine system and a concrete temperature stress testing method, and more particularly to a concrete temperature stress testing machine based on a walk-in environment simulation laboratory system, being capable of directly measuring deformation of concrete and having a function of temperature deformation self-compensation, and a testing method using the concrete temperature stress testing machine.

BACKGROUND

A concrete temperature stress testing machine (TSTM) may simulate the development of temperature stress and deformation of concrete under different restraint degrees and different temperature histories in a laboratory. The TSTM regulates and controls the temperature of the interior of concrete through changing the testing environment temperature, thereby controlling the development of temperature stress thereof. There are two cross-heads on both ends of concrete specimen, the cross-head at one end is a fixed cross-head and the other is a movable cross-head. When a tiny deformation of shrinkage or expansion takes place on concrete, an electric motor enables the concrete to return to the designated position by adjusting the movable cross-head, thereby the restraint conditions is achieved. The measuring deformation accuracy of the concrete specimen determines the accuracy and reliability of testing results. From the above, a temperature simulating method and a deformation measuring method of the TSTM are the technical key points that influence the performance of the TSTM.

Currently, two types of the concrete temperature control means for TSTM are mainly provided: one type is using a fluid-cooled temperature control formwork, which controls the temperature history of concrete by adjusting the temperature of the flowing fluid in the formwork, the other type is using an air-cooled environmental chamber, of which the concrete specimen is placed into the small environmental chamber, and the temperature of the concrete specimen is affected by adjusting the temperature and flowing of the air in the environmental chamber. However, at the present, both the two types of temperature control methods are only focusing on controlling the temperature near the concrete test specimen, which has some deficiencies.

A first deficiency is that, the concrete test specimen is placed in the environment of controllable temperature, however a frame and a steel shaft of the TSTM is placed in the natural environment of the laboratory, and then influenced by the environmental temperature fluctuation in the laboratory, the frame and the steel shaft of the testing machine will produce a temperature deformation, thereby influencing the deformation and strained of concrete. Taking the room temperature fluctuation of 1° C. as an example, the deformation of 12με will come about approximately concerning the steel shaft made from ordinary steel, while the threshold value controlled by the full restraint deformation of concrete is generally only 5 or 2με, the temperature deformation of the steel frame due to the environmental temperature fluctuation even exceeds the given threshold value adjusted by the concrete deformation, therefore the concrete deformation value measured by this method is not accurate.

A second deficiency is that, by the temperature control method of using the water-cooled formwork, the formwork and the concrete specimen are hard to be separated apart, the friction between the formworks and the concrete specimen will make an impact on the stress and deformation measurement during the concrete temperature stress test. In addition, a gap between the concrete formwork and the moveable cross-head should be reserved, thereby a synchronous temperature control between the concrete around the cross-head and the concrete of the middle portion contacting the formwork will not be achieved, so that a temperature gradient will be produced between the concrete around the cross-head and the concrete of the middle portion, resulting in an uneven axial temperature deformation.

A third deficiency is that, restricted by small environmental chamber, the deformation measured by the movable cross-head is utilized to present the concrete deformation. The method neglects the influence of machine rigidity and the gaps between connecting portions, so the measured deformation has much error.

A fourth deficiency is that, because the TSTM mainly consists of the steel shaft portion, the frame portion and the concrete specimen portion, the thermal expansion coefficient of each portion is different, and the temperature environment thereof is different as well, so the temperature deformation of each portion is discordant, the deformation result measured by a deformation sensor is a result containing the temperature deformation of the overall system. The temperature deformation of the system is mainly contributed by the deformation of testing machine frame and the steel shaft.

A fifth deficiency is that, concrete is an artificial material having discrete properties, in order to evaluate the material properties thereof accurately, multiple test specimens should be performed in parallel. If using the temperature simulation means of small environmental chamber or temperature formwork, it is difficult to ensure that multiple testing machines are placed in the same environment, while the synchronous control of multiple testing machines can't be achieved, thereby both the representativeness and the application universality of the testing result will be influenced.

In general, the TSTM which uses the technology of temperature control formwork or small environmental chamber can't achieve the aim that the multiple testing machines perform the test at the same time under the same temperature environment. The measured deformation can't represent the true deformation of concrete because of being influenced by rigidity of the testing machine and environment temperature. Errors of the testing results are relatively large, and even the incorrect testing phenomenon and conclusion will be obtained.

SUMMARY

Embodiments of the present disclosure seek to solve at least one of the problems existing in the related art to at least some extent. For that reason, the present disclosure provides a concrete temperature stress testing machine system based on a walk-in environment simulation laboratory system, which can achieve a synchronous control over multiple concrete temperature stress testing machines and a more accurate measurement of deformation. The present disclosure also provides a concrete temperature stress testing method using the concrete temperature stress testing machine.

Specifically, the present disclosure provides a concrete temperature stress testing machine system, including a concrete temperature stress testing machine and a walk-in environment simulation laboratory system, in which the concrete temperature stress testing machine is disposed in the walk-in environment simulation laboratory system, the concrete temperature stress testing machine includes: a testing machine host including a rear fixed end, a front fixed end, and a pair of steel shafts connected between the rear fixed end and the front fixed end; a concrete test specimen area including a moveable cross-head, a fixed cross-head, and a left side formwork, a bottom formwork and a right formwork connected between the moveable cross-head and the fixed cross-head. The front fixed end and the fixed cross-head are connected through a fixed end connecting ferrule, the rear fixed end and the moveable cross-head are connected through a load cell and a moveable end connecting ferrule, an outer side of the rear fixed end are connected to a servo motor; the steel shaft is made from No. 4J36 invar whose thermal expansion coefficient $\alpha_1$ is $0.5\sim2.5\times10^{-6}$m/° C.; the rear fixed end, the front fixed end, the fixed end connecting ferrule and the moveable end connecting ferrule are made from No. 4J36 invar whose thermal expansion coefficient $\alpha_1$ is $0.5\sim2.5\times10^{-6}$m/° C.; the fixed cross-head, the moveable cross-head, and the load cell are made from No. 45 steel whose thermal expansion coefficient $\alpha_2$ is $10\sim12\times10^{-6}$m/° C.

Further, a total length $L_1$ of the steel shaft is 3120 mm~3450 mm; a total length $L_2$ of the rear fixed end, the front fixed end, the fixed end connecting ferrule and the moveable end connecting ferrule is 1190 mm~1320 mm; a total length $L_3$ of the fixed cross-head, the moveable cross-head, and the load cell is 210 mm~300 mm; the dimension relationship meets $\alpha_1*L_2+\alpha_2*L_3=\alpha_1*L_1$.

Thus, the objective of temperature deformation self-compensation may be achieved.

Further, the concrete temperature stress testing machine may further include: an upper deformation measuring system including: two upper embedded rods located above the concrete test specimen area, in which an end of the upper embedded rod extends out the concrete test specimen area, the other end of the upper embedded rod extends into the concrete test specimen area and is provided with an embedded part having a cross-shaped section; an upper deformation sensor disposed to an upper portion of one of the upper embedded rods; an upper extending rod having a first end connected to the upper deformation sensor and a second end connected to the other one of the upper embedded rods; a left side deformation measuring system including: two left side embedded rods located at a left side of the concrete test specimen area, in which an end of the left side embedded rod extends out the concrete test specimen area, the other end of the left side embedded rod extends into the concrete test specimen area and is provided with an embedded part having a cross-shaped section; a left side deformation sensor disposed on the end, extending out the concrete test specimen area, of one of the left side embedded rods; a left side extending rod having a first end connected to the left side deformation sensor and a second end connected to the other one of the left side embedded rods; a right side deformation measuring system including: two right side embedded rods located at a right side of the concrete test specimen area, in which an end of the right side embedded rod extends out the concrete test specimen area, the other end of the right side embedded rod extends into the concrete test specimen area and is provided with an embedded part having a cross-shaped section; a right side deformation sensor disposed on the end, extending out the concrete test specimen area, of one of the right side embedded rods; a right side extending rod having a first end connected to the right side deformation sensor and a second end connected to the other one of the right side embedded rods.

Further, the left side and the right side deformation measuring systems each may further include an elastic adjusting assembly. The elastic adjusting assembly includes: two threaded baffle rings fitted over the side embedded rod and spaced from each other, in which positions of the two threaded baffle rings along an axial direction of the side embedded rod are adjustable and the threaded baffle ring adjacent to the side formwork abuts against an outer side surface of the side formwork; and an adjusting spring fitted over the side embedded rod and abutting against the two threaded baffle rings therebetween.

The concrete temperature stress testing machine further includes two T-shaped positioning fixtures, in which the T-shaped positioning fixtures are disposed perpendicularly to the left side formwork and the right side formwork and connected to the left side formwork and the right side formwork through bolts, and a middle convex portion of the T-shaped positioning fixture is connected to the upper embedded rod.

Further, a testing method using the concrete temperature stress testing machine according to the present disclosure includes the following steps: S1: adjusting a left side formwork, a bottom formwork and a right side formwork to proper positions, and mounting an upper embedded rod through a T-shaped positioning fixture, and mounting a left side embedded rod and right side embedded rod through an elastic adjusting assembly; S2: pouring concrete into a concrete test specimen area, and vibrating and tamping the concrete, so that an upper embedded part, a left side embedded part and a right side embedded part are located in the concrete test specimen area; S3: adjusting and mounting an upper extending rod, an upper deformation sensor, a left side extending rod, a left side deformation sensor, a right side extending rod and a right side deformation sensor; S4: demoulding after concrete is hardened, using the upper deformation sensor and the side deformation sensor to detect the deformation of concrete, and obtaining a testing deformation control value by detection and analysis, so as to achieve a feedback control.

In the step S4, a temperature $T_0$ at the beginning of installation and an environment temperature $T_t$ during the testing phase are recorded, and a formula $\varepsilon=\varepsilon_0-\alpha(T_t-T_0)$ is used to amend the deformation measured by the upper deformation sensor and the side deformation sensor, in which Co refers to a concrete deformation measured before a temperature amendment and $\alpha$ refers to a comprehensive thermal expansion coefficient of the testing machine.

Further, in the step S4, $(\varepsilon_A+\varepsilon_B+\varepsilon_C)/3$ is configured to be the testing deformation control value, in which $\varepsilon_A$, $\varepsilon_B$, and $\varepsilon_C$ refer to deformation values of the upper deformation sensor, the left side deformation sensor and the right side deformation sensor respectively after temperature compensation and amendment.

Additional aspects and advantages of embodiments of present disclosure will be given in part in the following descriptions, become apparent in part from the following descriptions, or be learned from the practice of the embodiments of the present disclosure.

DETAILED DESCRIPTION

Reference will be made in detail to embodiments of the present disclosure. The embodiments described herein with reference to drawings are explanatory, illustrative, and used to generally understand the present disclosure. The embodiments shall not be construed to limit the present disclosure.

Figure 1:
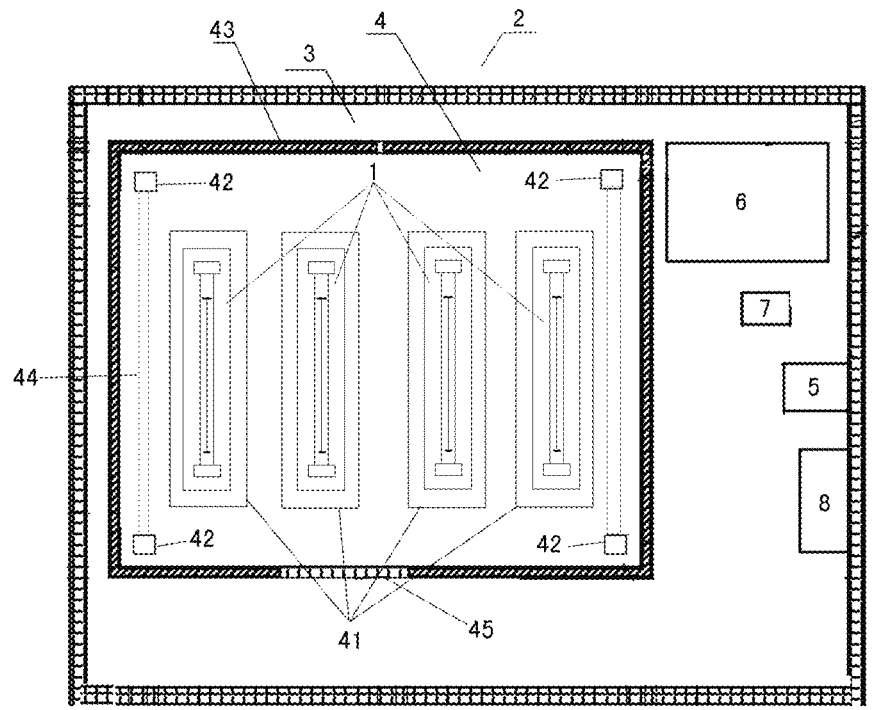
FIG. 1 is a plane schematic view of a concrete temperature stress testing machine system according to embodiments of the present disclosure.

Referring to FIG. 1, a concrete temperature stress testing machine system using a walk-in environment simulation laboratory according to embodiments of the present disclosure includes a concrete temperature stress testing machine 1 and a walk-in environment simulation laboratory system 2. The walk-in environment simulation laboratory system 2 includes an outer laboratory 3, a walk-in environment simulation laboratory 4 disposed within the outer laboratory 3, and a host control cabinet 5, a compressor set room 6, an environment room control cabinet 7 and a computer 8 disposed between the outer laboratory 3 and the walk-in environment simulation laboratory 4.

The environment room control cabinet 7 is provided with an environment simulation control unit, the environment simulation control unit includes a temperature simulation module, a humidity simulation module, a carbonization simulation module, a spray simulation module and an illumination simulation module.

Figure 2:
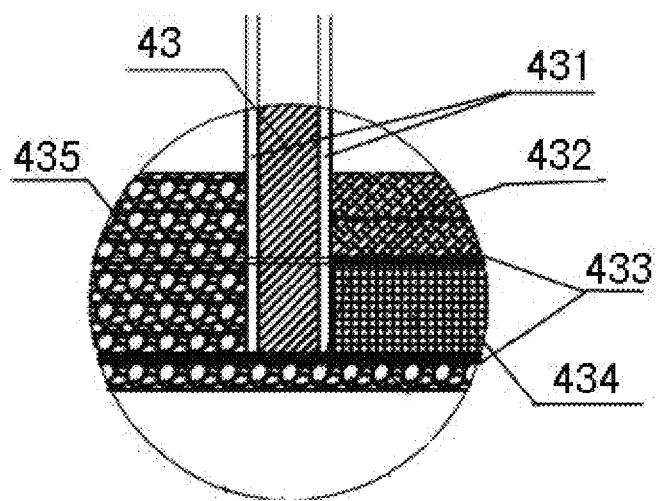
FIG. 2 is a partially enlarged view of a foundation of a walk-in environment simulation laboratory in the concrete temperature stress testing machine system according to embodiments of the present disclosure.

Referring to FIG. 2, in order to prevent a foundation from transferring heat, the foundation of a wall 43 of the walk-in environment simulation laboratory 4 uses a heat preservation and waterproof structure design; and an inner side of the foundation of the wall 43 of the walk-in environment simulation laboratory 4 includes a ferroconcrete layer 432, a waterproof layer 433, a heat preservation layer 433, an a concrete layer 435 successively from up to down. In order to reduce the unnecessary cost and procedures, an outer side of the foundation of the wall 43 is filled with the concrete layer 435 completely. In order to enhance the heat preservation effect of the walk-in environment simulation laboratory 4, the wall 43 of the walk-in environment simulation laboratory 4 is configured to be a polyurethane warehouse board, and a rubber isolation layer 431 is provided between the inner and outer sides of the wall 43 of the walk-in environment simulation laboratory 4.

The walk-in environment simulation laboratory 4 is provided with an entrance 45 for the entry of the concrete temperature stress testing machine, and the walk-in environment simulation laboratory 4 may accommodate a plurality of concrete temperature stress testing machines at the same time. In a specific embodiment of the present disclosure, the walk-in environment simulation laboratory 4 is provided with four concrete temperature stress testing machines arranged in parallel, i.e. these four concrete temperature stress testing machines are placed in the same environmental simulation atmosphere, the restraint condition of each testing machine is set according to a test requirement of itself, and the four testing machines carry out tests in the same environment, such that the temperature stress deformation data measured by each testing machine under the same environment condition may be contrasted and analyzed, enabling the testing result to have a higher analogy ability and a broader application scope.

In addition, steel ingots 42 are embedded in four corners of the walk-in environment simulation laboratory 4 respectively, so that the steel ingot 42 serves as a fulcrum to install a hoisting device of a concrete test specimen mould. Moreover in order to facilitate movement of the hoisting device among the respective steel ingots 42, a hoisting device track 44 is connected among the steel ingots 42.

The computer 8 is electrically connected with a controller in the host control cabinet 5, the host control cabinet 5 transmits the received concrete deformation data to the computer 8, and the data is analyzed and processed by the software of the computer 8. The controller in the host control cabinet 5 is also electrically connected with an environment simulation control unit in the environment room control cabinet 7; the environment simulation control unit in the environment room control cabinet 7 is electrically connected with a compressor set in the compressor set room 6; the compressor set room 6 and the environment room control cabinet 7 are electrically connected with the walk-in environment simulation laboratory 4. Relevant testing parameters are set through the software of the computer 8, the commands are released to the controller in the host control cabinet 5, and then the host control cabinet 5 transfers the commands to the environment simulation control unit in the environment room control cabinet 7, so as to control the temperature simulation module, the humidity simulation module, the carbonization simulation module, the spray simulation module, the illumination simulation module and other modules of the environment simulation control unit. Thus the temperature simulation module, the humidity simulation module, the carbonization simulation module, the spray simulation module, the illumination simulation module and other modules set the temperature, the humidity, the carbonization, the spray, the illumination and other environmental conditions of the walk-in environment simulation laboratory 4, and adjust the temperature in the walk-in environment simulation laboratory 4 in real time through the compressor set in the compressor set room 6. Therefore, the concrete temperature stress test may not only simulate the environment temperature and humidity, but also simulate the carbonization, the spray, the illumination and other environmental conditions, enabling the environment conditions of the concrete temperature stress test of the concrete temperature stress testing machine system to be more authentic and practical.

Figure 3:
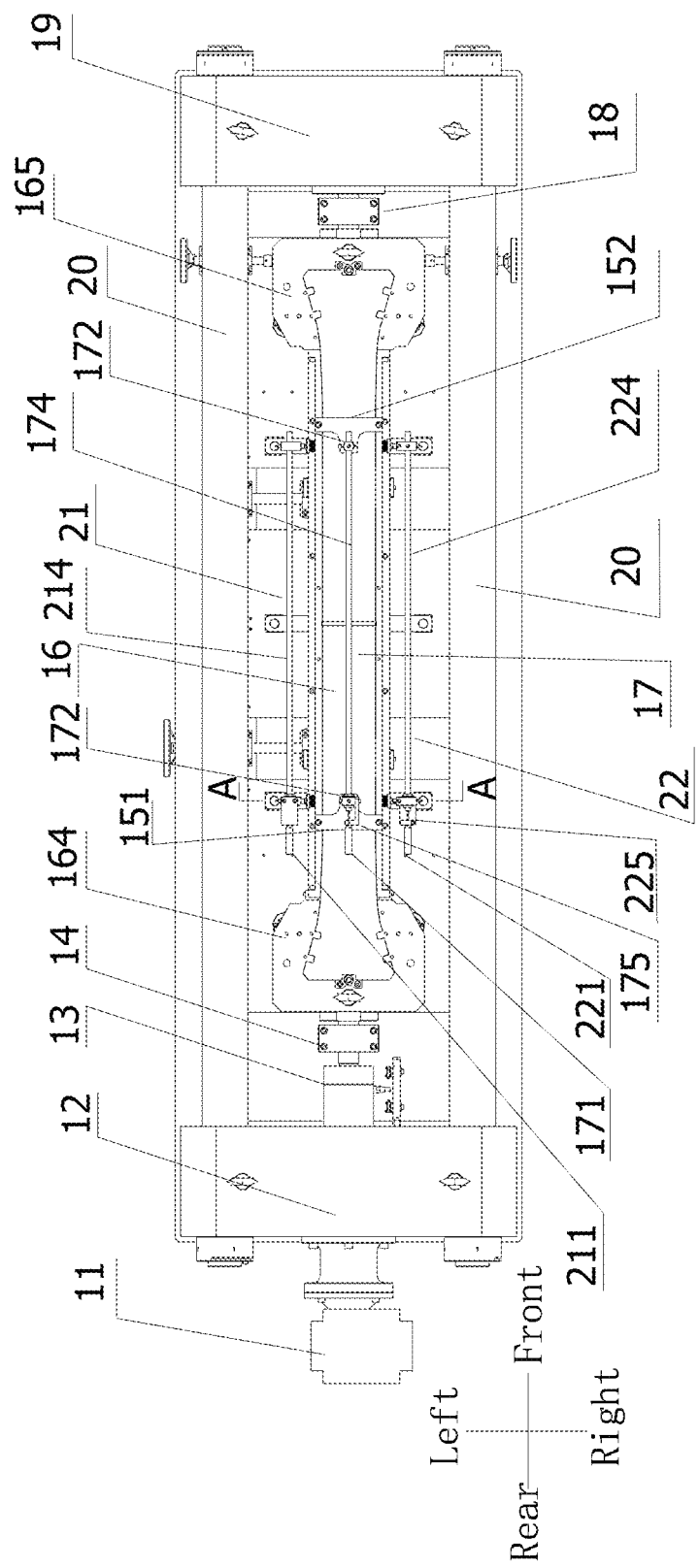
FIG. 3 is a top view of a concrete temperature stress testing machine according to embodiments of the present disclosure.
Figure 4:
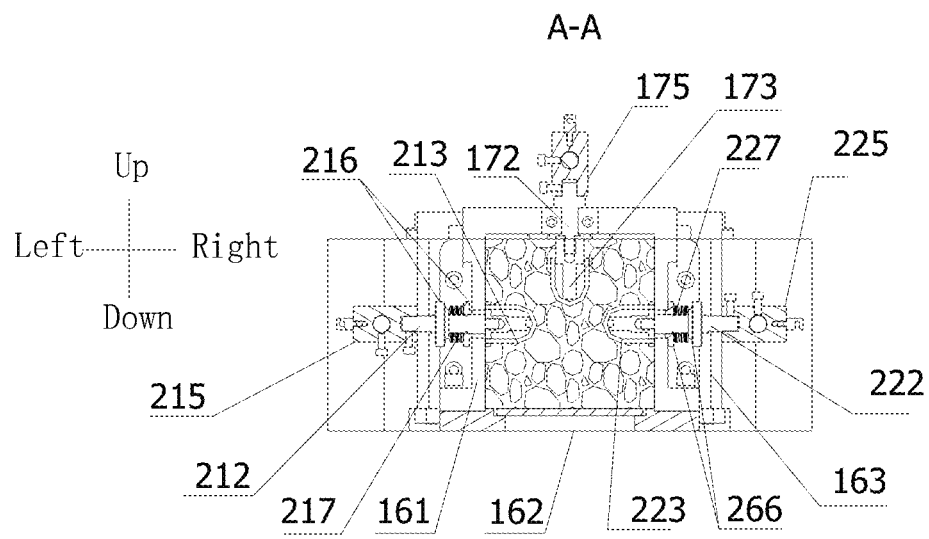
FIG. 4 is a sectional view of a concrete temperature stress testing machine in A-A direction according to embodiments of the present disclosure.
Figure 5:
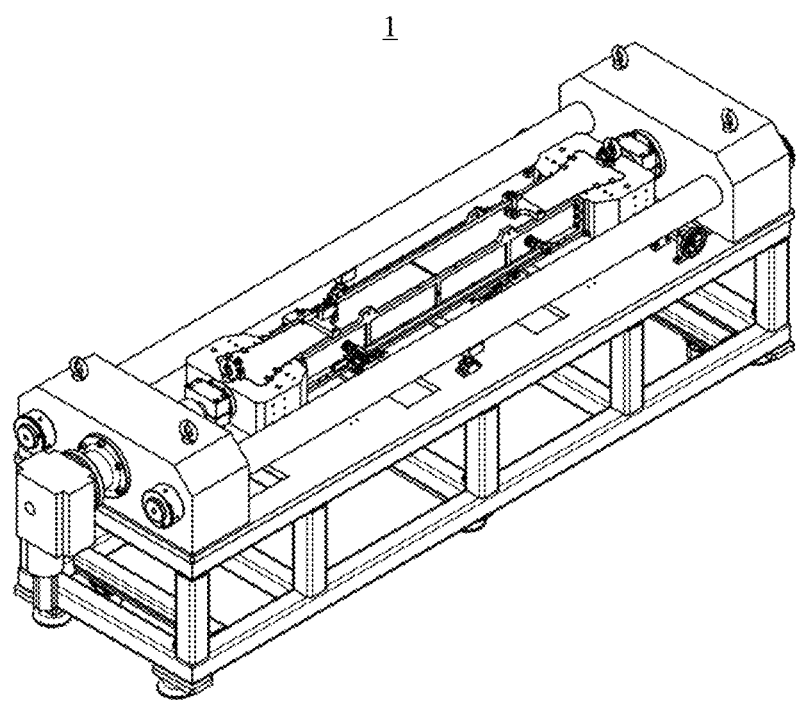
FIG. 5 is a perspective schematic view of a concrete temperature stress testing machine according to embodiments of the present disclosure.

Referring to FIGS. 3 and 4, the concrete temperature stress testing machine 1 according to embodiments of the present disclosure includes: a testing machine host, including a rear fixed end 12, a front fixed end 19, and a pair of steel shafts 20 connected between the rear fixed end 12 and the front fixed end 19; and a concrete specimen area 16, including a moveable cross-head 164, a fixed cross-head 165, and a left side formwork 161, a bottom formwork 162 and a right side formwork 163 connected between the moveable cross-head 164 and the fixed cross-head 165. The front fixed end 19 and the fixed cross-head 165 are connected through a fixed end connecting ferrule 18, the rear fixed end 12 and the moveable cross-head 164 are connected through a load cell 13 and a moveable end connecting ferrule 14, and an outer side of the rear fixed end 12 is connected to a servo motor 11. The steel shaft 20 is made from No. 4J36 invar whose thermal expansion coefficient $\alpha_1$ is $0.5{\sim}2.5\times10^{-6}$m/° C., and a total length $L_1$ thereof is 3120 mm~3450 mm; the rear fixed end 12, the front fixed end 19, the fixed end connecting ferrule 18 and the moveable end connecting ferrule 14 are made from No. 4J36 invar whose thermal expansion coefficient $\alpha_1$ is $0.5{\sim}2.5\times10^{-6}$m/° C., and the total length $L_2$ thereof is 1190 mm~1320 mm; the fixed cross-head 165, the moveable cross-head 164, and the load cell 13 are made from No. 45 steel whose thermal expansion coefficient axis $10{\sim}12\times10^{-6}$m/° C., and the total length $L_3$ is 210 mm~300 mm.

The above-mentioned dimension relationship meets $\alpha_1*L_2+\alpha_2*L_3=\alpha_1*L_1$. In the process of the concrete temperature stress test, the environment temperature fluctuation of 1° C. is be taken as an example, so as to make a detailed description of the temperature deformation of the concrete temperature stress testing machine.

When $\alpha_1=1.5\times10^{-6}$m/° C., $\alpha_2=11.59\times10^{-6}$m/° C., $L_1=3270$ mm, $L_2=1258.8$ mm, $L_3=257\ 2$ mm, the temperature deformation generated by the steel shaft 20 is: $\Delta L_1=\alpha_1\times\Delta T\times L_1=1.5\times10^{-6}\times1\times3270\times10^{-3}=4.905$; the temperature deformation generated by the rear fixed end 12, the front fixed end 19, the fixed end connecting ferrule 18 and the moveable end connecting ferrule 14 is: $\Delta L_2=\alpha_1\times\Delta T\times L_2=1.5\times10^{-6}\times1\times1258.8\times10^{-3}=1.882$; the temperature deformation generated by the fixed cross-head 165, the moveable cross-head 164, and the load cell 13 is: $\Delta L_3=\alpha_2\times\Delta T\times L_3=11.59\times10^{-6}\times1\times260.8\times10^{-3}=3.02$.

It can be seen that, the total temperature deformation generated by various steel portions of the concrete temperature stress testing machine is 4.905−1.882−3.023=0 μm. The impact of the steel deformation generated by outside temperature variations on the concrete test specimen may be omitted, thereby achieving the objective of temperature deformation self-compensation.

Further, the concrete temperature stress testing machine according to embodiments of the present disclosure may also include an upper deformation measuring system 17, a left side deformation measuring system 21 and a right side deformation measuring system 22.

The deformation measuring system 17 includes: two upper embedded rods 172, an upper deformation sensor 171 and an upper extending rod 174. The two upper embedded rods 172 are located above the concrete test specimen area 16 separately; an end of the upper embedded rod 172 extends out the concrete test specimen area 16, while the other end of the upper embedded rod 172 extends into the concrete test specimen area 16 and is provided with an embedded part 173 having a cross-shaped section. Thus, the embedded part 173 having the cross-shaped section may increase the area in contact with the concrete and the stressed area, which is beneficial to the deformation coordination between the concrete and the embedded rod, thereby improving the testing accuracy.

The upper deformation sensor 171 is disposed to an upper portion of one of the upper embedded rods 172. As shown in FIG. 3 and FIG. 4, one of the upper embedded rods 172 is connected with the upper deformation sensor 171 through an upper deformation sensor clamp 175. An end of the upper extending rod 174 is connected to the upper deformation sensor 171, and the other end of the upper extending rod 174 is connected to the other upper embedded rod 172.

One of the upper embedded rods 172 is connected with and positioned by a middle convex portion of a T-shaped positioning fixture 151. The T-shaped positioning fixture 151 is disposed perpendicular to the left side formwork 161 and the right side formwork 163, and connected with the two side formworks through bolts. The other upper embedded rod 172 is connected and positioned through a T-shaped positioning fixture 152 by the same way.

The left side deformation measuring system 21 has an arrangement basically similar to that of the upper deformation measuring system 17, and also includes two left side embedded rods 212, a left side deformation sensor 211 and a left extending rod 214. One of the left side embedded rods 212 has a first end extending into the concrete test specimen area 16 and connected with a left side embedded part 213 and a second end connected with the left side deformation sensor 211 through a left side deformation sensor clamp. Further the left side deformation measuring system also includes an elastic adjusting assembly, and the elastic adjusting assembly includes two threaded baffle rings 216 and an adjusting spring 217. The adjusting spring 217 is fitted over the left side embedded rod 212, and is located between and abuts against the two threaded baffle rings 216. The two threaded baffle rings 216 are fitted over the left side embedded rod 212 and spaced from each other, positions of the two threaded baffle rings 216 along an axial direction of the left side embedded rod 212 are adjustable, and the threaded baffle ring adjacent to the left side formwork 161 abuts against an outer side surface of the left side formwork 161. Thus, an elastic force of the adjusting spring 217 may be changed through adjusting the two threaded baffle rings 216, thereby preventing removal of the left side formwork 161 from affecting the position of the left side embedded rod 212, and further improving the deformation testing accuracy.

Likewise, the other left side embedded rod 212 is connected with the corresponding left side embedded part 213, the corresponding threaded baffle rings 216 and adjusting spring 217 in the same connecting manner as mentioned above. One end of the left side extending rod 214 is connected to the left side deformation sensor 211, and the other end thereof is connected to the other left side embedded rod 212.

The right side deformation measuring system 22 has a basically same arrangement as the left side deformation measuring system 21, and also includes two right side embedded rods 222, a right side deformation sensor 221 and a right extending rod 224; the difference between them is just that they are disposed at the left and right sides of the concrete test specimen area 16 respectively. One of the right side embedded rods 222 has a first end extending into the concrete test specimen area 16 and connected with a right side embedded part 223 and a second end connected with the right side deformation sensor 221 through a right side deformation sensor clamp. The right side deformation measuring system also includes an elastic adjusting assembly, and the elastic adjusting assembly includes two threaded baffle rings 226 and an adjusting spring 227. The adjusting spring 227 is fitted over the right side embedded rod 222, and is located between and abuts against the two threaded baffle rings 226. The two threaded baffle rings 226 are fitted over the right side embedded rod 222 and spaced from each other, positions of the two threaded baffle rings 226 along an axial direction of the right side embedded rod 222 are adjustable, and the threaded baffle ring adjacent to the right side formwork 163 abuts against an outer side surface of the right side formwork 163. Thus, tan elastic force of the adjusting spring 227 may be changed through adjusting the two threaded baffle rings 226, thereby preventing removal of the right side formwork 163 from affecting the position of the right side embedded rod 222, and further improving the deformation testing accuracy.

The other right side embedded rod 222 is connected with the corresponding right side embedded part 223, the corresponding threaded baffle rings 226 and adjusting spring 227 in the same connecting manner as mentioned above. One end of the right side extending rod 224 is connected to the right side deformation sensor 221, and the other end thereof is connected to the other right side embedded rod 222.

The concrete during deformation may drive the upper embedded rods 172, the left side embedded rods 212 and the right side embedded rods 222 to move, which may be measured by the sensors 171, 211 and 221, so that the true deformation of the concrete may be measured in such a manner of embedding an rod in the concrete test specimen area 16, so as to reduce the system errors generated during the deformation transmission. Compared with the method of measuring the displacement of the moveable cross-head 164, the true deformation of the concrete may be measured directly and the result is more direct and accurate.

A concrete temperature stress testing method for measuring the deformation by using the concrete temperature stress testing machine system according to embodiments of the present disclosure is described in the following, and the testing method includes the following steps.

S1: the left side formwork 161, the right side formwork 162 and the bottom formwork 163 are adjusted to proper positions; the upper embedded rods 172 are mounted through the T-shaped positioning fixtures 151 and 152, the left side embedded rod 212 is mounted through the threaded baffle rings 216 and the adjusting spring 217, and the right side embedded rod 222 is mounted through the threaded baffle rings 226 and the adjusting spring 227.

S2: the concrete is poured into the concrete test specimen area 16, and vibrated and tamped, so that the embedded parts 173, 213 and 223 are located in the concrete test specimen area.

S3: the upper extending rod 174, the upper deformation sensor 171, the left side extending rod 214, the left side deformation sensor 211, the right side extending rod 224 and the right side deformation sensor 221 are mounted and adjusted.

S4: after the concrete is hardened, the concrete is demoulded; the sensors 171, 211 and 221 are utilized to detect the deformation of the concrete, and a testing deformation control value is obtained by detection and analysis, so as to achieve a feedback control.

Further, in the step S4, a temperature $T_0$ at the beginning of installation and an environment temperature $T_t$ during the testing phase are recorded, and a formula $\varepsilon = \varepsilon_0 - \alpha(T_t - T_0)$ is employed to amend the deformation measured by the sensors 171, 211 and 221, in which Co refers to a concrete deformation measured before a temperature amendment, and $\alpha$ refers to a comprehensive thermal expansion coefficient of the testing machine. During the step S4, $(\varepsilon_A + \varepsilon_B + \varepsilon_C)/3$ is configured as the testing deformation control value, in which $\varepsilon_A$, $\varepsilon_B$, and $\varepsilon_C$ refer to deformation values of the upper deformation sensor 171 and two side deformation sensors 211 and 221 respectively after the temperature compensation and amendment. Thus, by using the manner of temperature self-compensation and amendment, the impact of the environment temperature variation on the measured deformation value may be eliminated, and the measured value has good long-term stability.

From the above, the concrete temperature stress testing machine system according to embodiments of the present disclosure is a concrete temperature stress testing machine having the function of temperature deformation self-compensation and being capable of directly measuring the deformation of concrete, which may effectively overcome the problems of the concrete temperature stress testing machine in the prior art, including that the measured deformation is not the true deformation of concrete and the measurement accuracy is not high and the like. Based on the walk-in environment simulation technology, the synchronous control over the plurality of testing machines may be achieved, and by placing the concrete test specimen and the deformation measuring system under the same testing environment, the impact of the temperature deformation will be self-compensated; moreover, the direct measurement of the true deformation of concrete has advantages of high accuracy and good long-term stability.

Other configurations and operations of the concrete temperature stress testing machine according to embodiments of the present disclosure are known to those skilled in the art, which will not be described in detailed herein.

In the specification, it is to be understood that terms such as "central," "longitudinal," "lateral," "length," "width," "thickness," "upper," "lower," "front," "rear," "left," "right," "vertical," "horizontal," "top," "bottom," "inner," "outer," "clockwise," and "counterclockwise" should be construed to refer to the orientation as then described or as shown in the drawings under discussion. These relative terms are for convenience of description and do not require that the present invention be constructed or operated in a particular orientation.

In the description of the present invention, "a plurality of" means two or more than two, unless specified otherwise.

In the present invention, unless specified or limited otherwise, the terms "mounted," "connected," "coupled," "fixed" and the like are used broadly, and may be, for example, fixed connections, detachable connections, or integral connections; may also be mechanical or electrical connections; may also be direct connections or indirect connections via intervening structures; may also be inner communications of two elements, which can be understood by those skilled in the art according to specific situations.

Reference throughout this specification to "an embodiment," "some embodiments," "one embodiment", "another example," "an example," "a specific example," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example," "in an example," "in a specific example," or "in some examples," in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A concrete temperature stress testing machine system comprising a concrete temperature stress testing machine and a walk-in environment simulation laboratory system, wherein the concrete temperature stress testing machine is disposed within the walk-in environment simulation laboratory system, wherein the concrete temperature stress testing machine comprises:
   a testing machine host comprising a rear fixed end, a front fixed end, and a pair of steel shafts connected between the rear fixed end and the front fixed end;
   a concrete test specimen area comprising a moveable cross-head, a fixed cross-head, and a left side formwork, a bottom formwork and a right formwork connected between the moveable cross-head and the fixed cross-head;
   wherein the front fixed end and the fixed cross-head are connected through a fixed end connecting ferrule, the rear fixed end and the moveable cross-head are connected through a load cell and a moveable end connecting ferrule, and an outer side of the rear fixed end is connected to a servo motor;
   wherein the steel shaft is made from No. 4J36 invar whose thermal expansion coefficient $\alpha_1$ is $0.5 \sim 2.5 \times 10^{-6}$ m/°C.; the rear fixed end, the front fixed end, the fixed end connecting ferrule and the moveable end connecting ferrule are made from No. 4J36 invar whose thermal expansion coefficient $\alpha_1$ is $0.5 \sim 2.5 \times 10^{-6}$ m/°C.; the fixed cross-head, the moveable cross-head, and the load cell are made from No. 45 steel whose thermal expansion coefficient $\alpha_2$ is $10 \sim 12 \times 10^{-6}$ m/°C.

2. The concrete temperature stress testing machine system according to claim 1, wherein:
   a total length $L_1$ of the steel shaft is 3120 mm~3450 mm;
   a total length $L_2$ of the rear fixed end, the front fixed end, the fixed end connecting ferrule and the moveable end connecting ferrule is 1190 mm~1320 mm;
   a total length $L_3$ of the fixed cross-head, the moveable cross-head, and the load cell is 210 mm~300 mm;
   the dimension relationship meets $\alpha_1*L_2+\alpha_2*L_3=\alpha_1*L_1$.

3. The concrete temperature stress testing machine system according to claim 1, wherein the concrete temperature stress testing machine further comprises:
   an upper deformation measuring system comprising: two upper embedded rods located above the concrete test specimen area, wherein an end of the upper embedded rod extends out the concrete test specimen area, the other end of the upper embedded rod extends into the concrete test specimen area and is provided with an embedded part having a cross-shaped section; an upper deformation sensor disposed to an upper portion of one of the upper embedded rods; an upper extending rod having a first end connected to the upper deformation sensor and a second end connected to the other one of the upper embedded rods;
   a left side deformation measuring system comprising: two left side embedded rods located at a left side of the concrete test specimen area, wherein an end of the left side embedded rod extends out the concrete test specimen area, the other end of the left side embedded rod extends into the concrete test specimen area and is provided with an embedded part having a cross-shaped section; a left side deformation sensor disposed on the end, extending out the concrete test specimen area, of one of the left side embedded rods; a left side extending rod having a first end connected to the left side deformation sensor and a second end connected to the other one of the left side embedded rods;
   a right side deformation measuring system comprising: two right side embedded rods located at a right side of the concrete test specimen area, wherein an end of the right side embedded rod extends out the concrete test specimen area, the other end of the right side embedded rod extends into the concrete test specimen area and is provided with an embedded part having a cross-shaped section; a right side deformation sensor disposed on the end, extending out the concrete test specimen area, of one of the right side embedded rods; a right side extending rod having a first end connected to the right side deformation sensor and a second end connected to the other one of the right side embedded rods.

4. The concrete temperature stress testing machine system according to claim 3, wherein the left side and the right side deformation measuring systems each further comprise an elastic adjusting assembly, and the elastic adjusting assembly comprises:
   two threaded baffle rings fitted over the side embedded rod and spaced from each other, wherein positions of the two threaded baffle rings along an axial direction of the side embedded rod are adjustable and the threaded baffle ring adjacent to the side formwork abuts against an outer side surface of the side formwork; and
   an adjusting spring fitted over the side embedded rod and abutting against the two threaded baffle rings therebetween.

5. The concrete temperature stress testing machine system according to claim 3, wherein the concrete temperature stress testing machine further comprises two T-shaped positioning fixtures, wherein the T-shaped positioning fixtures are disposed perpendicular to the left side formwork and the right side formwork and connected to the left side formwork and the right side formwork through bolts, and a middle convex portion of the T-shaped positioning fixture is connected to the upper embedded rod.

6. A testing method using a concrete temperature stress testing machine according to claim 5, comprising the following steps:
   S1: adjusting a left side formwork, a bottom formwork and a right side formwork to proper positions, mounting an upper embedded rod through a T-shaped positioning fixture, and mounting a left side embedded rod and a right side embedded rod through an elastic adjusting assembly;
   S2: pouring concrete into a concrete test specimen area, and vibrating and tamping the concrete, so that an upper embedded part, a left side embedded part and a right side embedded part are located in the concrete test specimen area;
   S3: adjusting and mounting an upper extending rod, an upper deformation sensor, a left side extending rod, a left side deformation sensor, a right side extending rod and a right side deformation sensor;
   S4: demoulding after concrete is hardened, using the upper deformation sensor and the side deformation sensor to detect deformation of concrete, and obtaining a testing deformation control value by detection and analysis, so as to achieve a feedback control.

7. The testing method according to claim 6, wherein in the step S4, a temperature $T_0$ at the beginning of installation and an environment temperature $T_t$ during a testing phase are recorded, and a formula $\varepsilon=\varepsilon_0-\alpha(T_t-T_0)$ is utilized to amend the deformation measured by the upper deformation sensor and the side deformation sensor, in which $\varepsilon_0$ refers to a concrete deformation measured before a temperature amendment and $\alpha$ refers to a comprehensive thermal expansion coefficient of the testing machine.

8. The testing method according to claim 6, wherein in the step S4, $(\varepsilon_A+\varepsilon_B+\varepsilon_C)/3$ is configured as the testing deformation control value, wherein $\varepsilon_A$, $\varepsilon_B$, and $\varepsilon_C$ refer to deformation values of the upper deformation sensor, the left side deformation sensor and the right side deformation sensor respectively after temperature compensation and amendment.

* * * * *